(12) United States Patent
Rahmel et al.

(10) Patent No.: US 11,070,550 B2
(45) Date of Patent: Jul. 20, 2021

(54) DEVICE FOR IDENTIFYING A PERSON AND A METHOD THEREOF

(71) Applicant: Well Being Digital Limited, Shatin (HK)

(72) Inventors: Juergen Harald Rahmel, Hong Kong (HK); Wong Ming Yip Wallace, Hong Kong (HK)

(73) Assignee: WELL BEING DIGITAL LIMITED, New Territories (HK)

( * ) Notice: Subject to any disclaimer, the term of this patent is extended or adjusted under 35 U.S.C. 154(b) by 0 days.

(21) Appl. No.: 15/755,491

(22) PCT Filed: Jan. 24, 2018

(86) PCT No.: PCT/CN2018/074022
§ 371 (c)(1),
(2) Date: Feb. 26, 2018

(87) PCT Pub. No.: WO2018/137662
PCT Pub. Date: Aug. 2, 2018

(65) Prior Publication Data
US 2019/0347386 A1    Nov. 14, 2019

(30) Foreign Application Priority Data
Jan. 28, 2017    (HK) .................................. 17101077.5

(51) Int. Cl.
*H04L 29/06*    (2006.01)
*G06F 3/01*    (2006.01)
(Continued)

(52) U.S. Cl.
CPC .......... *H04L 63/0861* (2013.01); *G06F 3/011* (2013.01); *G06F 3/017* (2013.01);
(Continued)

(58) Field of Classification Search
CPC ........... G06F 21/32; G06F 3/011; G06F 3/017
(Continued)

(56) References Cited

U.S. PATENT DOCUMENTS 9,165,216 B2 * 10/2015 Angell .................... G06F 21/32
2006/0074280 A1    4/2006 Martis et al.
(Continued)

FOREIGN PATENT DOCUMENTS

| CN | 101442933 A | 5/2009 |
| CN | 204633806 U | 9/2015 |

(Continued)

OTHER PUBLICATIONS

Lamonaca, "Health parameters monitoring by smartphone for quality of life improvement", May 2015, Elsevier, pp. 82-94 (Year: 2015).*

(Continued)

*Primary Examiner* — Taghi T Arani
*Assistant Examiner* — Gregory A Lane (57) ABSTRACT

A device having a fingerprint reader and a first heart rate monitor which are co-located such that a person's heart rate is obtained at the same time as this fingerprint. The device is integral to yet another heart rate monitor for monitoring the performance of the person in exercise. The readings of the other heart rate monitor correlates to the readings of the first heart rate monitor if the person whose fingerprint is read is the same person wearing the second heart rate monitor, in which case the fingerprint is deemed acceptable for identifying the person. Other biometric identification besides fingerprint can be used such as iris recognition.

12 Claims, 10 Drawing Sheets

(51) Int. Cl.
*G06F 21/32* (2013.01)
*G06K 9/00* (2006.01)
*H04W 12/02* (2009.01)
*H04W 12/03* (2021.01)
*H04W 12/065* (2021.01)

(52) U.S. Cl.
CPC ......... *G06F 21/32* (2013.01); *G06K 9/00013* (2013.01); *H04W 12/02* (2013.01); *H04W 12/03* (2021.01); *H04W 12/065* (2021.01)

(58) Field of Classification Search
USPC .............................................................. 726/2
See application file for complete search history.

(56) References Cited

U.S. PATENT DOCUMENTS

| | | | |
|---|---|---|---|
| 2007/0057800 A1 | 3/2007 | Coughlin et al. | |
| 2009/0039241 A1 | 2/2009 | Ueki | |
| 2010/0217102 A1* | 8/2010 | LeBoeuf | A61B 5/00 600/310 |
| 2012/0019361 A1* | 1/2012 | Ben Ayed | G06F 21/32 340/5.83 |
| 2012/0154117 A1* | 6/2012 | Nice | G06F 21/32 340/5.82 |
| 2014/0241597 A1 | 8/2014 | Leite | |
| 2014/0266696 A1* | 9/2014 | Addison | A61B 5/1171 340/539.12 |
| 2014/0343443 A1* | 11/2014 | Yuen | G06F 19/3418 600/509 |
| 2015/0170292 A1 | 6/2015 | Fung et al. | |
| 2017/0039358 A1* | 2/2017 | Yuen | A61B 5/0002 |
| 2018/0358113 A1* | 12/2018 | Cronin | G06F 19/32 |

FOREIGN PATENT DOCUMENTS

| | | |
|---|---|---|
| CN | 106037706 A | 10/2016 |
| CN | 106067243 A | 11/2016 |
| EP | 1358842 A1 | 11/2003 |
| EP | 3037036 A1 | 6/2016 |

OTHER PUBLICATIONS

Foreign Communication from a Related Counterpart Application, European Extended Search Report dated Mar. 29, 2019, European Application No. 18700444 filed on Jan. 24, 2018.

Foreign Communication from a Related Counterpart Application, Hong Kong Search Report dated Mar. 3, 2017, Hong Kong Application No. 17101077.5 filed on Feb. 7, 2017.

Foreign Communication from a Related Counterpart Application, International Search Report dated Apr. 28, 2018, International Application No. PCT/CN2018/074022 filed on Jan. 24, 2018.

* cited by examiner

DEVICE FOR IDENTIFYING A PERSON AND A METHOD THEREOF

FIELD OF INVENTION

The present invention relates to a person authentication device and method. In particular, the invention relates to a device which can be used to ascertain that the person wearing or using the device is indeed the person as authenticated.

BACKGROUND OF THE INVENTION

Wearable devices have been proposed for monitoring physical performance of people in exercise or sport. People using such a device normally just wear the device on their wrist, waist, chest and so on. Some of these devices contain an accelerometer to count the number of steps the person has taken in a cross-country run or the number of stokes he has executed in a swim, or to observe the height to which he has jumped. Some of these devices are able to monitor the heart rate or temperature of the person, and may raise an alarm when the person appears to be at the end of his endurance or performance tolerance. Furthermore, these devices may contain a GPS respondent to observe the distance the person has covered in a long distance sport.

These devices may be used to record competition between persons who are physically remote from each other. The performance of the persons may be recorded in real time and displayed on the wearable device worn by each person. In this way, the persons are able to tell many steps each of them has taken and the distance each has covered. The problem with such wearable devices is that they can be taken off and worn by someone else instead of the intended person. Someone else may wear the device for a person to take part in a competition in place of the person.

Biometrics authentication methods have been proposed to authenticate the person wearing such a device. For example, the device comprises a fingerprint reader which is used to authenticate the person. However, this method is not fool proof. Someone who is taking part in a competition in place of a person may wear the device while the person provide the fingerprint to be read.

Therefore, it is desirable to provide an authentication method for verifying the identity of the actual person wearing such wearable devices.

SUMMARY OF THE INVENTION

In a first aspect, the invention proposes a device for identifying a person comprising: a physiological monitor; a biometric identity reader; wherein the biometric identity reader and the physiological monitor are configured such that the biometric identity reader reads biometric information of the person and the physiological monitor reads physiological information of the person at the same time.

Reading biometric information at the same time as reading physiological data using the same device provides the possibility that the physiological data be verified as belonging to the person identified by the biometric information.

Preferably, the physiological monitor is adjacent the biometric identity reader; such that the physical distance between physiological monitor and the biometric identity reader prevents the physiological monitor and the biometric identity reader from being applied separately to more than one person at the same time. For example the physiological monitor and the biometric identity reader are in the same device housing which is sized to be placed on the same part of the body of the person. A smaller housing ensures that embodiments of the invention are used at the same time and on the same person; the physiological monitor cannot be physically applied on one person while the biometric identity reader is applied on another person.

Preferably, the physiological monitor monitors the heart beat pattern of the person. The term 'heart beat pattern' is used to include heart rate but may also refer other kinds of physiological observations made on the heart. For example, instead of heart rate, the 'heart beat pattern' may be a peak to peak magnitude.

Optionally, the device is in communication with a second physiological monitor; the biometric identity reader and the physiological monitor of the device, and the second physiological monitor are configured such that the biometric identity reader reads biometric information of the person, the physiological monitor reads physiological information of the person and the second physiological monitor reads physiological information of the person at the same time.

This provides the possibility that, from one set of physiological data, any number of 'second' physiological monitors worn by the identified person may be verified cascadingly as being worn by the same person, provided that the same physiological data read of all these devices match. Once these other 'second' physiological monitors are verified as being worn by the same person, different functions of these 'second' physiological monitors may be employed with confidence that they are applied on the identified person.

Optionally, the device is in communication with the second physiological monitor wirelessly. In such embodiments, the device is a smart phone having a fingerprint scanner which can read the heart rate pattern from a person's fingertip, and the second physiological monitor is a device worn by the person. The person may wear the second physiological monitor on his wrist, ankle, ear, head, chest or even internally in his body (such as a swallowed device in his intestines). The wireless communication protocol can be Wi-Fi, Bluetooth™, infrared and so on.

Preferably, however, the device is physically integral with the second physiological monitor, the integrated device having a dimension which prevents the physiological monitor, the biometric identity reader and the second physiological monitor from being applied onto different persons. This helps to ensure the integrity of embodiment physically in the sense that the embodiments have to be applied onto the same person who may be identified by the biometric identity reader.

Preferably, the biometric identity reader is a fingerprint reader. Alternatively, the biometric identity reader is a biometric heartbeat pattern reader, such as a biometric ECG monitor. In some embodiments, the biometric identity reader and the physiological monitor are both provided as one, in the form of a camera, the camera positioned to be capable of being looked into by the eye of the person Preferably, the device further comprises a belt for strapping to the wrist of the person.

Alternatively, the device is an earphone or ear bud which can be inserted into a person's ear canal, in which case the second physiological monitor may be a light based blood flow monitor installed in the ear phone or ear bud.

Preferably, the second physiological monitor is a light based blood flow monitor installed in an ear phone.

Optionally, the biometric identity reader is an accelerometer, for monitoring characteristic mannerism of the person using the device, the characteristic mannerism of the person being useable as a behavioural biometric identification.

In a second aspect, the invention proposes a physiological monitor, which is capable of obtaining a first set of physiological data read from a person; supplying the first set of physiological data to be matched to a second set of physiological data read from the same person; the first set of physiological data and the second set of physiological data read from the same person at the same time.

Typically, the person from whom the second set of physiological data is read has been authenticated. Therefore, devices containing the physiological monitor may be used for monitoring the performance of a person wearing such a device, and the person may be authenticating by matching the first set of physiological data and the second set of physiological data.

This provides the advantage that different physiological monitors may be provided or sold to the person separately and yet benefit from being able to obtain the second set of physiological data for matching to the first set of physiological data. In this way, as long as the second set of physiological data has been verified as having been obtained from an authenticated person, the first set of physiological data may be relied upon as having been read from the authenticated person Preferably, the first set of physiological data is read from the person in real time. Therefore, the second set of physiological data is also read from the person in real time. This allows improved identity security in that the second set of physiological data is not pre-recorded.

Optionally, the physiological monitor is a light based blood flow monitor installed in an ear phone.

Preferably, the physiological monitor is capable of encrypting physiological data in real time using biometric data of the person. Different persons may use the same device, but each of them separately and independent authenticated as they use the device in turn.

In yet a further aspect, the invention proposes a method of authenticating physiological information of person comprising the steps of: providing a first physiological monitor; providing a biometric identity reader; the biometric identity reader reading biometric information of the person and the first physiological monitor reading physiological information of the person at the same time; authenticating the biometric information of the person in order to accept the physiological information as belonging to the person.

Preferably, the biometric identity reader and the first physiological monitor are physically constrained preventing from being applied separately to more than one person at the same time.

Preferably, the biometric information of the person is keystroke patterns characteristic of the person typing on a keyboard.

Preferably, the method comprises the further steps of: providing a second physiological monitor; the second physiological monitor reading physiological information of the person; if the physiological information read by the first physiological monitor correlates to the physiological information read by the second physiological monitor; accepting yet further physiological information read by the second physiological monitor as belonging to the person.

Preferably, the method comprises the further step of encrypting the further physiological information read by the second physiological monitor using the biometric information of the person.

In a further aspect, the invention proposes a physiological monitor and a biometric identity reader co-located to read from the same part of a living body. The part of the body may be a fingertip or the eye. Typically, but not necessarily, the physiological monitor is a pulse reader, and the biometric identity reader is a fingerprint reader if the part of the body is the fingertip or biometric identity reader is an iris scanner if the part of the body is the eye. Being co-located, preferably in the same physical housing to prevent the physiological monitor and the biometric identity reader from be separated, ensures that the information is read from the same person. In this way, both the readings from the physiological monitor and the biometric identity reader can be said to originate from the same person with certainty.

BRIEF DESCRIPTION OF THE FIGURES

It will be convenient to further describe the present invention with respect to the accompanying drawings that illustrate possible arrangements of the invention, in which like integers refer to like parts. Other arrangements of the invention are possible, and consequently the particularity of the accompanying drawings is not to be understood as superseding the generality of the preceding description of the invention.

DETAILED DESCRIPTION OF EMBODIMENTS

Embodiment 1

Figure 1:
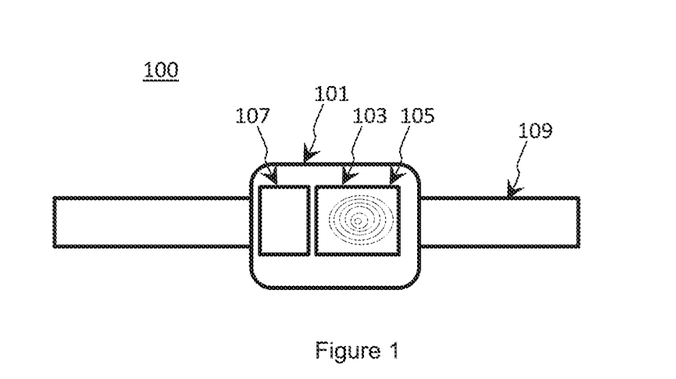
FIG. 1 is an illustrate of a first embodiment.
Figure 2:
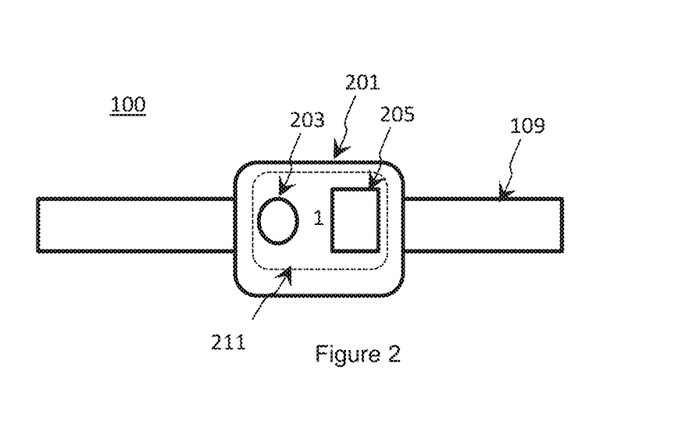
FIG. 2 is an illustration of the embodiment of FIG. 1 in a different view.
Figure 3:
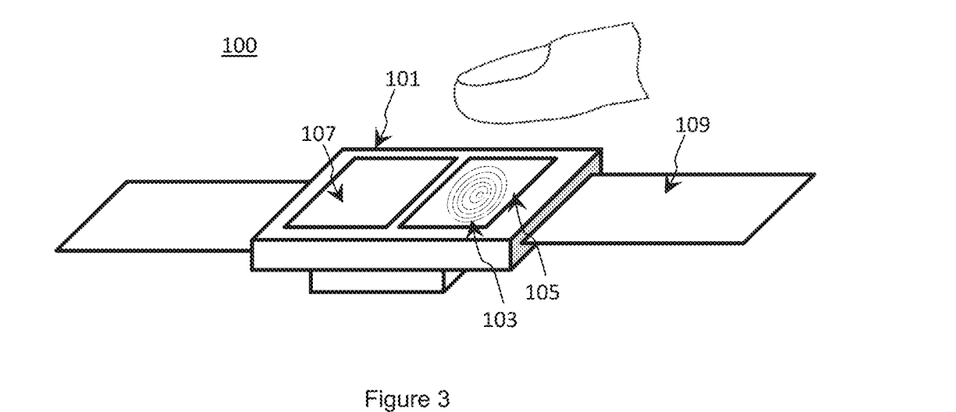
FIG. 3 illustrates the embodiment of FIG. 1 in perspective view.
Figure 4:
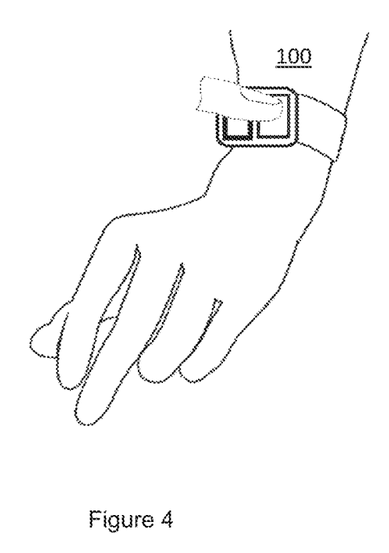
FIG. 4 illustrates the embodiment of FIG. 1 in use.

FIG. 1 to FIG. 4 show a first embodiment 100, which is a device that may be worn on the wrist of a person. The top face 101 of the device is shown in FIG. 1, i.e. it faces away from the wrist when worn. The underside 201 is shown in FIG. 2, i.e. the face which is in contact with the wrist of the person if worn. FIG. 3 shows the embodiment 100 in perspective view. FIG. 4 shows the embodiment 100 when worn by the person.

Both the top face 101 and the bottom face 201 are each provided with a light-based heart rate monitor. The preferred type of light base heart rate monitor is the PPG sensor (photoplethysmography).

The top PPG sensor 103 in FIG. 1, i.e. the PPG sensor on the top face 101 of the embodiment 100, is superimposed with a fingerprint reader 105 such that the tip of a finger is able to cover the top PPG sensor 103 and the fingerprint reader 105 at the same time.

'Superimposition' means the top PPG sensor 103 and the fingerprint reader 105 are laid one over the other. However, the meaning of 'superimposition' also includes any configuration in which the top PPG sensor 103 and the fingerprint reader 105 are placed in such close proximity such that a person's fingertip is able to cover over both the top PPG sensor and the finger print reader at once. In other words, the top PPG sensor 103 and the fingerprint reader 105 may also be adjacent or next to one another.

Next to the fingerprint reader 105 is a screen 107 for displaying information. However, in other embodiments, the fingerprint reader 105, the top PPG sensor 103 and the display screen 107 are laid one over the other in order to maximise the size of the screen 107 over the top face 101 of the device.

The embodiment 100 is provided with wrist straps 109. The person wears the embodiment 100 by strapping it over his wrist so that the bottom PPG sensor 211 is placed snugly against the person's skin. A typical PPG sensor comprises at least one light source 203 such as an LED (light emitting diode), which is illustrated by a circle in FIG. 2, and at least one corresponding optical sensor 205 normally placed next to the light source 203, which is illustrated by a square in FIG. 2. A rectangular dashed line in FIG. 2 around the optical sensor 205 and a light source 203 represents the bottom PPG sensor 211 as a whole.

Figure 2A:
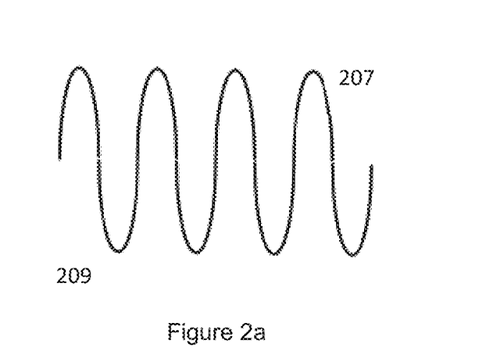
FIG. 2a illustrates a heart rate signal observable by the embodiment of FIG. 1.

The light frequency of the light source 203 is such that blood in the wrist skin and wrist tissue is able to absorb the light. Light from the light source 203 which has transmitted through the skin and tissue of a person is normally pulsating. The pulsation is cyclical and virtually periodic, corresponding to the flushing of blood into the skin and tissue as it is pumped by the heart. FIG. 2a schematically illustrates the pulsating pattern of PPG sensor light propagation through a person's skin and tissue. The peaks 207 in the signal are moments when the heart is relaxed and wrist tissue is relatively depleted of blood, such that more light propagates through the wrist to reach the optical sensor. The troughs 209 in the signal are moments when the heart has contracted and wrist tissue is relatively full of blood, such that less light propagates through the wrist to reach the optical sensor 205 because most of the light has been absorbed by blood. The optical sensor 205 monitors this pulsation, which can be used to determine the pattern of the heart beat of the person against whose skin is the PPG sensor placed.

FIG. 1 does not illustrate the top PPG in its components of an optical sensor and a light source, but the skilled reader should understand that these components make up the top PPG nevertheless.

The fingerprint reader 105 superimposed with the top PPG sensor 103 provides the possibility that the person to identified himself as the person who is indeed wearing the embodiment 100.

To authenticate himself as the person wearing the embodiment 100, the person places his index finger over the fingerprint reader 105 and the top PPG sensor 103 at the same time. This is illustrated in FIG. 3 and FIG. 4.

As the top PPG sensor 103 is practically in the same location as the fingerprint reader 105, while the fingerprint of the person's index finger is being scanned, the top PPG sensor 103 is also reading the person's heart beat pattern from the index finger. At the same time, the bottom PPG sensor also monitors the person's heart beat pattern from the person's wrist.

The heart beat pattern is the same throughout the person's body. Therefore, the heart beat pattern read by the top PPG sensor 103 and heart beat pattern read by the bottom PPG sensor 211 should be identical if the person wearing the embodiment 100 is the same person who has placed this finger onto the fingerprint reader 105. Accordingly, if the heart beat patterns observed by each of the two PPG sensors in the embodiment 100 correlate, it is deemed that the person who is wearing the embodiment 100 is also the person whose fingerprint has been scanned. In this case, the scanned fingerprint is deemed acceptable for verifying the identity of the person. The embodiment 100 then transmits the scanned fingerprint to a server wirelessly for verification. A copy of the person's fingerprint has been scanned and recorded in the server in advance, which may therefore be used as a template for matching the scanned fingerprint transmitted from the embodiment 100 for verifying the person's identity.

Alternatively, the fingerprint scanned by the embodiment 100 is matched with a copy of the person's fingerprint which has been pre-stored inside a memory within the embodiment 100 for verifying the person's identity.

If the heart beat patterns observed by each of the two PPG sensors in the embodiment 100 do not correlate, it is deemed that the person who is wearing the embodiment 100 is not the person whose fingerprint has been scanned. Therefore, the fingerprint scanned by the embodiment 100 is not accepted for verifying the identity of the person.

Typically, the person identity is assumed to be verified and the embodiment worn by the person as long as the bottom PPG sensor 211 has not detected itself being moved away from the person. For example, if the optical sensor 205 of bottom PPG sensor 211 detects bright ambient light, the embodiment 100 will assume that the embodiment 100 has been taken off the person's wrist. Alternatively, if the embodiment 100 detects that the heart rate of the person has ceased to be detectable for a period of time, the embodiment 100 will also assume that the embodiment 100 has been taken off the person's wrist. In these cases, the person's identify needs to be verified again using the aforementioned procedure.

Subsequently, the person can begin exercising and his heart rate and exercise performance can be recorded by the embodiment 100. If the embodiment contains an accelerator, the person's steps can be counted. If the embodiment contains a GPS, the person's location can be monitored. This data can be transmitted to the server which the embodiment 100 is in wireless communication with to be stored under the person's profile.

The embodiment is useable to monitor the performance of different people in different parts of the world all wearing an embodiment 100. The performance of these different people performance can be recorded and compared in real time by the server to facilitate a remote competition.

Accordingly, the embodiment 100 provides a possibility of ensuring that the identity of the person who is actually wearing the embodiment is authenticated.

Other technologies may be used instead of that of the PPG sensor such as those based on infrared light, electrodes to monitor electrical signals and so on. These do not require elaboration here.

In a variation of the embodiment 100, once the person has been authenticated, the biometric data is used to encrypt any data which is sent over to the server by the embodiment. Where the server has a copy of the biometric data of the person, the server is able to decrypt the data. In this way, different persons may use the same device, but each of them may be separately and independent authenticated as they use the device in turn. Their physiological data and other information which is collected by the device may be securely released to the server without fear of being intercepted wirelessly and used. This allows the same embodiment to be used by multiple users to obtain very sensitive and personal physiological data for medical record and yet retain security of information from each other and unknown third parties. Virtually, as the physiological data is obtained continually from the person wearing the embodiment, the encryption of each packet of data of physiological data is done in real time.

Accordingly, the embodiment 100 includes a method of performing real time data encryption using a person's biometric data. Preferably, the biometric data has been first verified as described.

Embodiment 2

Figure 5:
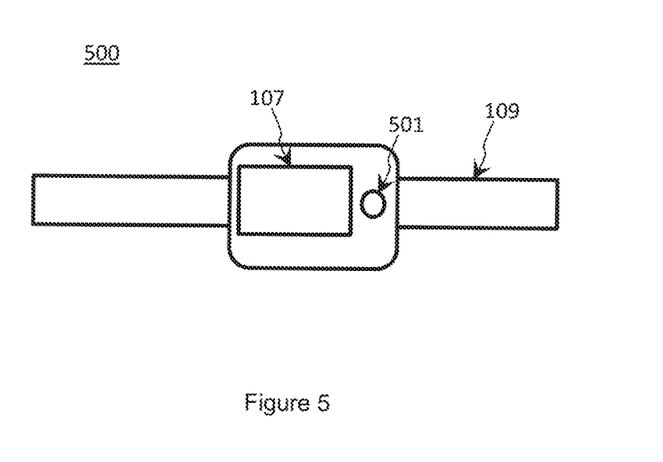
FIG. 5 is an illustrate of a second embodiment.

FIG. 5 illustrates another embodiment 500. In this embodiment, the person's authentication is obtained not by his fingerprint but by biometric eye recognition. This may be Iris recognition. The iris has a complex pattern which is unique to every person. The pattern is stable and can be seen from some distance. Iris recognition can be done using a video camera to capture the iris pattern in near infrared illumination.

In a variation of this embodiment, the biometric eye recognition is retinal blood vessel pattern recognition. However, this not the preferred method as the retina requires a more in-depth scan of the eye.

This embodiment 500 is also a wrist worn device and a bottom PPG sensor 211 is still used to monitor the blood flow in the person's wrist. However, FIG. 5 shows the embodiment 100 comprising a camera 501 in place of the fingerprint reader 105 and the top PPG sensor 103 in the first embodiment. This is because the camera 501 is able to capture an image of the iris for identification of the person, as well as observe the pulsations of blood vessel in the retina to monitor the heart beat pattern of the person.

Figure 6:
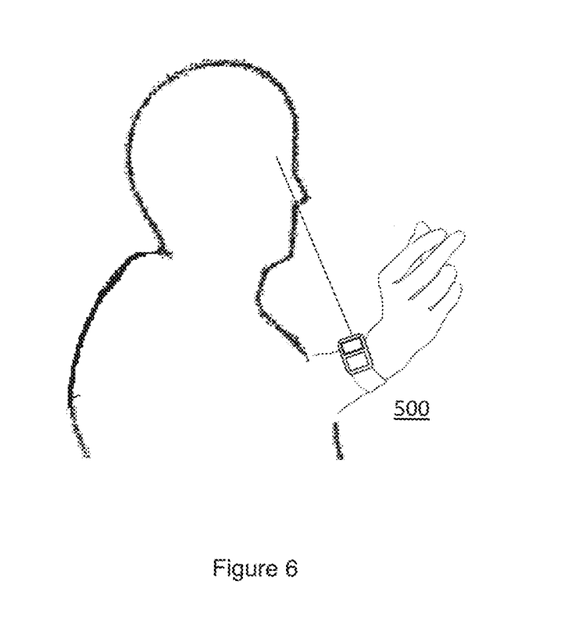
FIG. 6 is an illustrate of the embodiment of FIG. 5 in use.

In use, the person wears the embodiment on this wrist, such that the bottom PPG sensor 211 is able to monitor heart beat pattern from the person's wrist. The person then looks into the camera 501, as illustrated in FIG. 6, in order that his iris pattern may be scanned and also that the heart beat pattern may be observed from the pulsating flow of blood in the blood vessels inside his eye. The light frequency used for monitoring blood flow in the eye is preferably selected to be near infrared for better sensitivity.

The heart beat pattern observed by the camera 501 from the pulsating blood flow in the person's eye and the heart beat pattern as observed by the bottom PPG sensor 211 from the person's wrist should be identical if the person wearing the embodiment 100 on his wrist is indeed the same person who has looked into the camera 501. If the two heart beat patterns are identical, it is deemed that the person who is wearing the embodiment is indeed the person whose iris pattern has been scanned. Therefore, the iris pattern is deemed accepted for verifying the identity of the person.

The embodiment 100 then transmits the iris pattern to a server wirelessly for verification. A copy of the person's iris pattern has been scanned and recorded in the server in advance, which may therefore be used as a template for matching the scanned iris pattern transmitted from the embodiment 100 for verifying the person's identity.

Alternatively, the iris pattern scanned by the embodiment 100 is matched with a copy of the person's iris pattern which has been pre-stored inside a memory within the embodiment 100 for verifying the person's identity.

Conversely, if the heart rate patterns are not identical, it is deemed that the person who is wearing the embodiment is not the person whose iris pattern has been scanned. Therefore, the iris pattern is rejected for verifying the identity of the person.

Typically, the person identity is assumed to be verified and the embodiment worn by the person as long as the bottom PPG sensor 211 has not detected itself being moved away from the person. For example, if the optical sensor 205 of bottom PPG sensor 211 detects bright ambient light, the embodiment 100 will assume that the embodiment 100 has been taken off the person's wrist. Alternatively, if the embodiment 100 detects that the heart rate of the person has ceased to be detectable for a period of time, the embodiment 100 will also assume that the embodiment 100 has been taken off the person's wrist. In these cases, the person's identify needs to be verified again using the aforementioned procedure.

Embodiment 3

Figure 7:
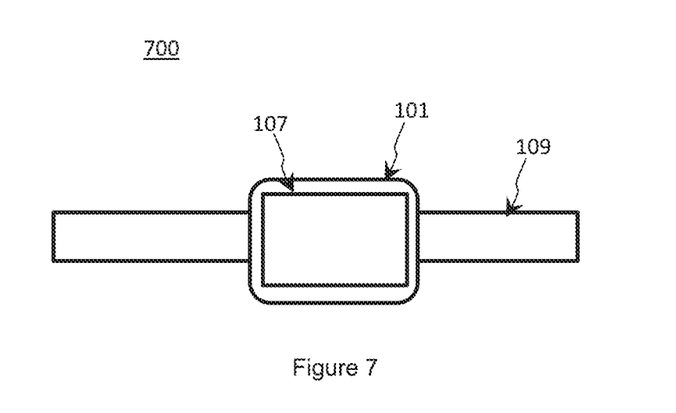
FIG. 7 is an illustrate of a third embodiment.
Figure 8:
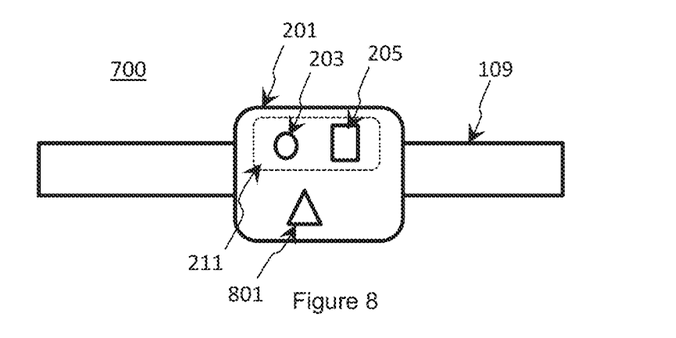
FIG. 8 is an illustration of the embodiment of FIG. 7 in a different view.

FIG. 7 and FIG. 8 shows another embodiment 700 comprising a miniature ECG (electrocardiogram) sensor instead of the fingerprint reader 105 of the first embodiment. The pattern of a heart beat signal obtained in an ECG has specific characteristics which are biometrically unique to every person.

In this embodiment 700, the fingerprint reader 105 and the top PPG sensor 103 in the first embodiment 100 are not required. Only the bottom PPG sensor 211 is needed for monitoring the heart beat pattern of the person from the person's wrist. As the ECG sensor is able to obtain heart beat signals, the ECG sensor fulfils both the role of a biometric authentication device, as well as that of a heart beat pattern monitor.

The ECG sensor 801 is shown in FIG. 8 placed on the bottom face 201 of the embodiment 700 in FIG. 8. That is, the ECG sensor 801 is located on the same side of the embodiment 700 as the bottom PPG sensor 211.

Accordingly, the top face 101 of the embodiment as shown in FIG. 7 can be fully occupied by a display, as a top PPG sensor no longer occupies the top face 101.

Figure 9:
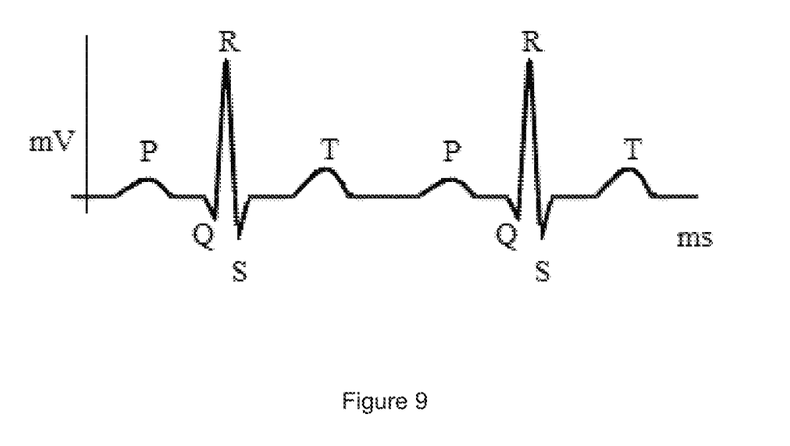
FIG. 9 illustrates a heart rate signal observable by the embodiment of FIG. 7.

FIG. 9 shows a standard cardiogram having several peaks which can be detected as electric signals from the different heart chambers, represented by PQRST. An ECG can identify a person using heartbeat sub-patterns (in particular the P, QRS, T, PQRS and QRST subsets of the standard ECG of a person), or even the full heartbeat waveform (Exploring Heartbeat Sub-patterns for Person Identification, Carreiras et. al., Portuguese Conference on Pattern Recognition 2013). Details of the technology used in an ECG sensor are not within the scope of this invention and therefore detailed elaboration of it is not necessary.

In use, the person wears the embodiment 700 on his wrist, such that the bottom PPG sensor 211 is able to monitor his heart beat pattern from the wrist. The ECG sensor 801 is also on the underside of the embodiment and therefore observes the ECG of the person from virtually the same part of the wrist. The heart beat pattern observed by the bottom PPG sensor 211 and the heart rate observed by the ECG sensor 801 should correlate, since they are read from the person. However, the bottom PPG sensor 211 is unable to collect fine details for biometric recognition like the ECG sensor 801. The bottom PPG sensor 211, on the other hand, is more rugged and robust, and is useable to monitor the heart beat pattern of the person over long period of time while he is engaging in strenuous activities. In contrast, a wearable ECG sensor is more delicate and may be obtaining too much information after the person has been verified or authenticated, which requires more intensive processing power. Furthermore, in most situations, there is no need for continual biometric identification.

Therefore, it is preferred to have both the bottom PPG sensor 211 and the ECG sensor 801 in the same embedment even though the ECG sensor may well by itself monitor the heart beat pattern of the person.

To authenticate himself as the person wearing the embodiment 700, the person merely needs to interact with the display screen 107 trigger an authentication process.

As the bottom PPG sensor 211 is practically in the same location as the ECG sensor 801, while the ECG-biometric identity of the person is being scanned, the bottom PPG sensor 211 is also reading the person's heart beat pattern from the wrist. The ECG-biometric identity of the person naturally contains the person's heart beat pattern.

The heart beat pattern read by the bottom PPG sensor 211 and heart beat pattern embodied in the ECG-biometric identity should be the same. Accordingly, the ECG-biometric identity is used for verifying the identity of the person. The embodiment 700 transmits the ECG-biometric identity 'to a server wirelessly for verification of the person. A copy of the person's ECG-biometric identity has been scanned and recorded in the server in advance, which may therefore be used as a template for matching the ECG-biometric identity transmitted from the embodiment 700 for verifying the person's identity.

Alternatively, the ECG-biometric identity scanned by the embodiment 100 is matched with a copy of the person's ECG-biometric identity which has been pre-stored inside a memory within the embodiment 700 for verifying the person's identity.

As with the earlier embodiments, the person identity is assumed to be verified and the embodiment worn by the person as long as the bottom PPG sensor 211 has not detected itself being moved away from the person.

Embodiment 4

Figure 10:
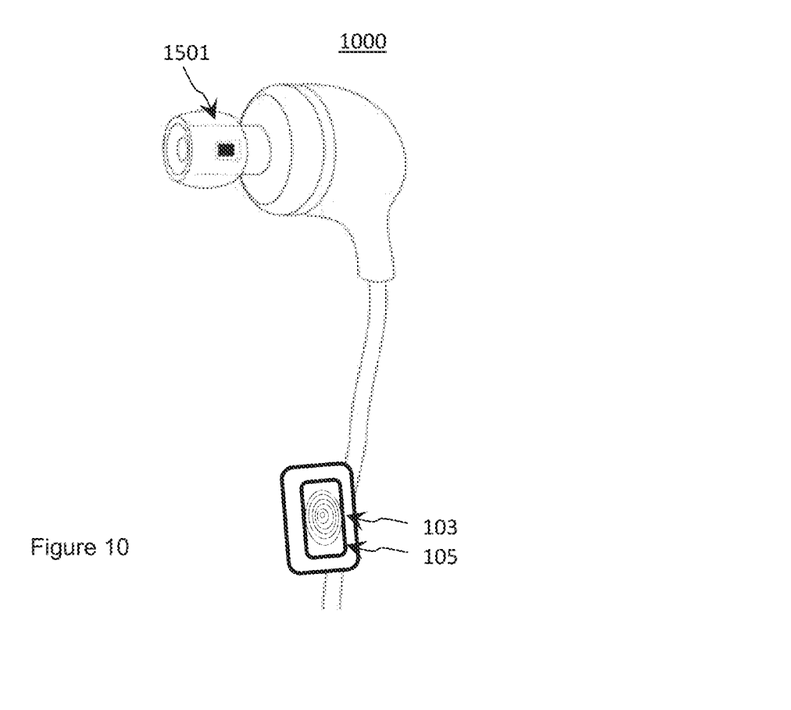
FIG. 10 is an illustrate of a fourth embodiment.
Figure 11:
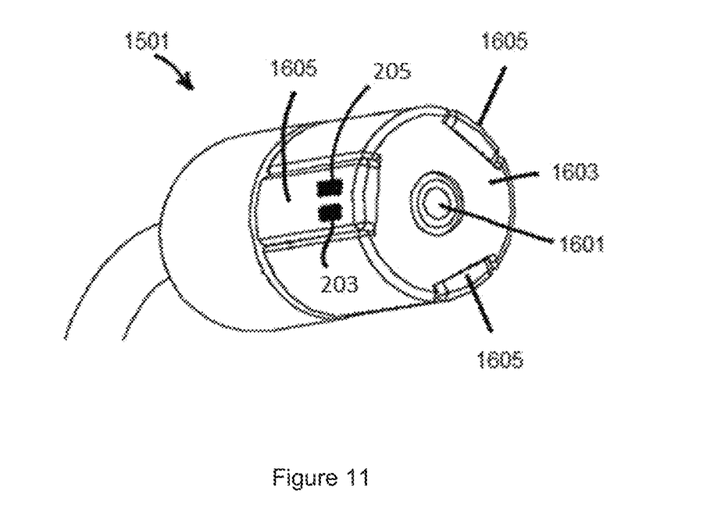
FIG. 11 is another illustration of the embodiment of FIG. 10.
Figure 12:
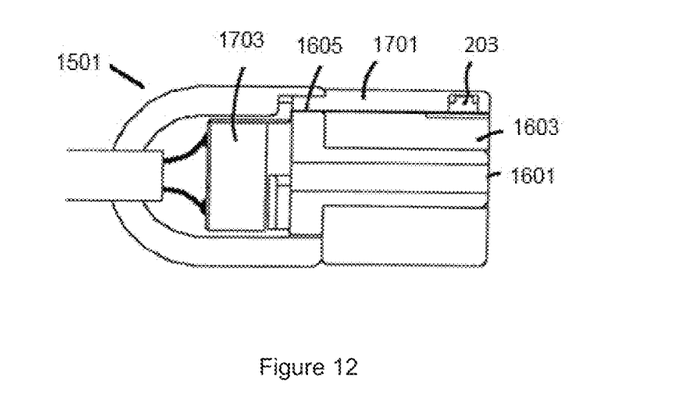
FIG. 12 is a different view of the embodiment of FIG. 11.

FIG. 10 shows yet another embodiment 1000, which is a smart earphone 1000 containing physiological sensors. FIG. 11 shows a close up of the ear bud 1501 of the smart earphone 1000 which is intended for insertion in the ear canal, stripped of the typical foam covering. FIG. 12 shows the same ear bud 1501 in a cross sectional side view.

The earphone 1000 comprises a light source 203 and an optical sensor 205 arranged in the ear bud 1501. Typically, the ear bud 1501 is made of a deformable resilient outer part 1701 sized to fit within the ear canal of a person. Within the ear bud 1501 is a speaker 1703, a hollow inner core 1601 for sound conduction from the speaker in to the ear, an resilient inner foam structure 1603 for softness and flexibility, thin wirings (not illustrated) for connection to the light source 203 and optical sensor 205. The resilient outer part 1701 provides increased comfort and protection of the light source 203 and optical sensors 205. The resilient inner foam 1603 may be compressed during insertion of the ear bud 1501 into the ear to provide further support in the ear canal. There are three sets 1605 of light source 203 and optical sensor 205 pairs, spaced 120 degree around the ear bud. One set is facing the reader showing clearly the light source 203 and optical sensor 205, while the other sets face away from the reader.

To monitor the heart beat pattern of the person wearing the earphone 100, the light source 203 transmit a light into the skin and tissue of the ear canal. As light propagates into the skin and tissue, some of the light is scattered and is diverted towards the optical sensor 205. Blood content in the ear canal affects the transmission of light. When there is more blood in the ear, more light is absorbed and less light is scattered towards the optical sensor 205. When there is less blood in the ear, less light is absorbed and more light is scattered towards the optical sensor 205. Therefore, the pumping of the heart is detectable by monitoring the transmission of light from the light source 203 through the skin and tissue, and to the optical sensor 205.

The earphone 1000 is capable of communicating with a server wirelessly to send physiological data of the person, the identity of the person and the GPS location of the earphone to the server.

FIG. 10 shows that along the wire leading up to the earphone 1000 is a housing which contains a fingerprint reader 105, which is co-located with a top PPG sensor 103, both arranged in a similar manner as that in the embodiment of FIG. 1. The underside of the housing does not have a PPG sensor, as the function of collecting heart beat pattern of the bottom PPG sensor is now provided in the ear bud 1501.

To identifying himself to the server which the smart earphone is in communication with, the person simply places his fingertip onto the fingerprint reader 105 and the PPG sensor 103 at once. The scanning of the person's fingerprint is done at the same time and from the same part of the finger as the PPG sensor 103 reads the person's heart beat pattern.

When the fingerprint reader 105 begins scanning the person's fingerprint, the sensors in the earphone are triggered to read the heart beat pattern of the person at the same time.

The heart beat pattern read from the finger and in the ear canal should be identical if the person wearing the ear bud is the same person who has placed this finger onto the fingerprint reader. Therefore, if the heart beat patterns observed by the PPG sensor 103 and the sensors in the earphone correlate, it is deemed that the person who is wearing the ear bud is actually the person whose fingerprint has been scanned. The scanned fingerprint is therefore deemed acceptable for use in verifying the identity of the person.

Conversely, if the heart rates as observed by the PPG sensor 103 and the sensors in the earphone do not correlate, it is deemed that the person who is wearing the ear bud is not the person whose fingerprint has been scanned. Therefore, the scanned fingerprint is rejected for verifying the identity of the person.

Typically, the person identify is assumed to be the same as long as the sensors in the ear bud do not detected that the ear bud has been taken out of the ear canal. For example, if the optical sensors in the ear bud detect bright ambient light, the smart earphone will determine that that indicates that the embodiment has been taken off the person's ear canal. in such a case, the person's identify needs to be verified again.

Embodiment 5

Figure 13:
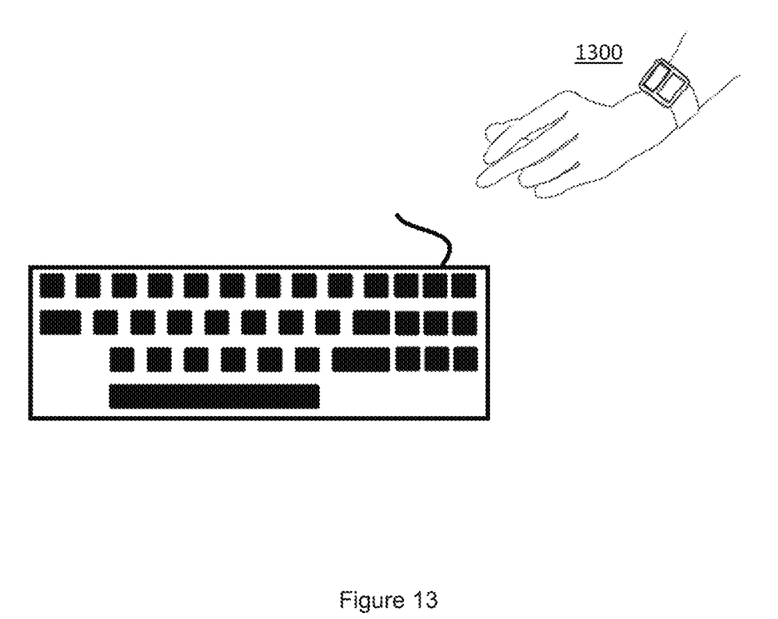
FIG. 13 illustrates yet another embodiment.

FIG. 13 illustrates yet another embodiment 1300. The embodiment 1300 is a wrist worn device containing the bottom PPG sensor (not visible in FIG. 13) to read the person's heart beat pattern from his wrist, similar to the embodiment 100 of FIG. 1, except that the embodiment 1300 now includes an accelerometer (not illustrated) to monitor movements of the wrist.

The biometric authentication of the person in this embodiment is behavioural instead of a physical attribute. In particular, the manner in which the person types a password has unique keystroke rhythm. That is, the accentuation of different strokes on different keys, the time period between typing on every two letters in the password and which of his hands does the person use for typing certain characters in the password and so on. The typing manner of a password has been found to be unique to every person.

When the person using this embodiment 1300 is about to type his password on the keyboard, the person triggers the embodiment 1300 to detect movements caused by the typing. At the same time, the embodiment 1300 is reading the heart beat pattern using the bottom PPG sensor at the person's wrist.

The computer also monitors the person's typing characteristics as the person enters his password, monitoring the keystroke rhythm, that is, the accentuation of different strokes on different keys (e.g. keyboards can detect accentuations as staccato and non-staccato typing), the time period between typing on every two letters in the password and so on. The computer is able to communicate with the device on the person's wrist wirelessly, such as by WiFi or Bluetooth™. Either the computer or the device, or both, are able to match the typing characteristics detected by the embodiment 1300 from the person's hand when he was entering the password with the typing characteristics sensed by the computer from the keyboard.

If the typing characteristics of those characters entered by that hand wearing the embodiment 1300 match the typing characteristics of those characters received by the computer (entered by that same hand), it shall be deemed that the embodiment is being worn by the person who has been identified the password. Subsequently, heart beat pattern obtained by the PPG sensor and any other physiological data, or movement data as provided by the embodiment 1300 are deemed as belonging the person as verified.

Alternatively, the person uses a smart phone instead of a computer to enter his password. The person enters his password into the smart phone using the hand wearing the embodiment 1300. If the typing characteristics of those characters entered by that hand wearing the embodiment 1300 match the typing characteristics of those characters received by the smart phone (entered by that same hand), it shall be deemed that the embodiment 1300 is being worn by the person who has been identified the password.

Embodiment 6

Figure 14:
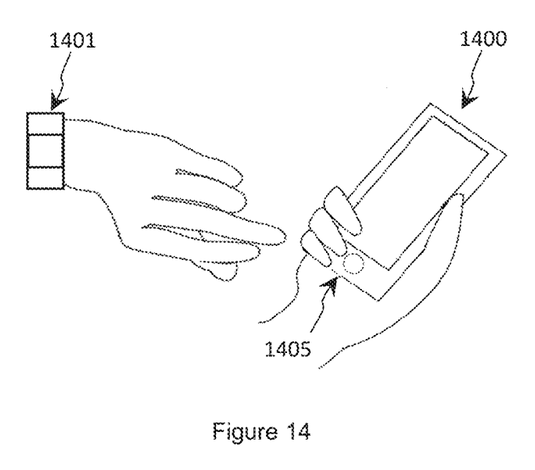
FIG. 14 illustrates yet another embodiment.

FIG. 14 shows another embodiment.

A person wears a sports monitoring device 1401 on this wrist. The sports monitoring device 1401 is similar to the embodiment of FIG. 1 in that it comprises a bottom PPG sensor 211 which may be used to monitor the blood flow in the person's wrist. However, the sports monitoring device 1401 does not have the fingerprint reader 105 superimposed with the top PPG sensor 103 of FIG. 1 for authenticating the person.

Instead, the sports monitoring device 1401 relies on a remote biometric authentication device 1400.

The remote biometric authentication device 1400 is provided for reading the person's fingerprint and heart beat pattern. Preferably, the remote biometric authentication device 1400 is a smart phone which comprises a fingerprint reader 1405 for unlocking the smart phone for user access. The fingerprint reader 1405 is superimposed with a PPG sensor such that a finger placed on the fingerprint reader 1405 to be scanned for fingerprint is also monitored for heart beat pattern at the same time by the PPG sensor.

Therefore, to use the sports monitoring device 1401, the person places his index finger on the fingerprint reader 1405 of the remote biometric authentication device 1400. The remote biometric authentication device is in wireless communication, such as by WiFi or Bluetooth™, with the sports monitoring device 1401.

The heart beat pattern read by fingerprint reader 1405 of the remote biometric authentication device 1400 from the person's finger and the heart beat pattern read by the bottom PPG sensor 211 in the sports monitoring device 1401 from the person's wrist should be identical or very similar, provided that the person wearing the sports monitoring device 1401 is indeed the same person who has placed this finger onto the fingerprint reader 1405. Accordingly, if the heart beat patterns matches, it is deemed that the person who is wearing the sports monitoring device 1401 is also the person whose fingerprint has been scanned by the remote biometric authentication device 1400. In this case, the scanned fingerprint is deemed acceptable for verifying the identity of the person.

Subsequently, the person can begin exercising and his heart rate and exercise performance can be recorded by the sports monitoring device 1401 and communicated to a server which is in wireless communication with the sports monitoring device 1401.

This embodiment illustrates how the biometric authentication device does not need to be physically integrated with the PPG sensor on the person's wrist. In variations of this embodiment, the remote biometric authentication device 1400 can be linked to the sports monitoring device 1401 by a physical wire for providing a communication channel between them.

Embodiment 7

Figure 15:
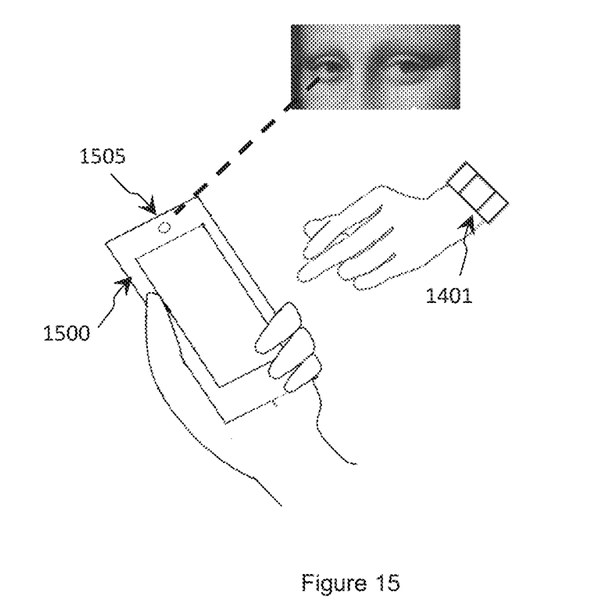
FIG. 15 illustrates yet another embodiment.

FIG. 15 illustrates a variation of the embodiment of FIG. 14, in which the fingerprint reader is replaced with a camera for iris biometric recognition.

A person wears a sports monitoring device 1401 on this wrist. The device 1401 is similar to the embodiment of FIG. 1 in that the device comprises a bottom PPG sensor 211 which may be used to monitor the blood flow in the person's wrist. However, the sports monitoring device 1401 does not have the fingerprint reader 105 superimposed with the top PPG sensor 103 of FIG. 1. Instead, the sports monitoring device 1401 relies on a remote biometric authentication device 1500.

The remote biometric authentication device 1500 is provided for reading the person's iris and also the person's heart beat pattern from blood vessels in his eye. Preferably, the remote biometric authentication device 1500 is a camera 1505 in a smart phone 1500.

Therefore, to use the sports monitoring device 1401, the person looks into the camera 1505. The remote biometric authentication device 1500 is in wireless communication, such as by WiFi or Bluetooth™, with the sports monitoring device 1401.

The heart beat pattern read by the remote biometric authentication device 1500 from the person's eye and the heart beat pattern read by the bottom PPG sensor 211 in the sports monitoring device 1401 from the person's wrist should be identical or very similar, provided that the person wearing the sports monitoring device 1401 is indeed the same person who looks into the camera 1505. Accordingly, if the heart beat patterns matches, it is deemed that the person who is wearing the sports monitoring device 1401 is also the person whose iris has been scanned by the remote biometric authentication device 1500. In this case, the scanned iris is deemed acceptable for verifying the identity of the person.

The embodiments illustrate how, by reading biometric information at the same time as physiological data such as heart rate pattern, may the physiological data be verified as belonging to the identified person. From one set of physiological data, any number of other devices worn by the same person may be verified in turn as being worn by the identified person if the physiological data of all these devices match. This allows remotely conducted sports or competition to be held without fear that the athlete or competitor has be replaced by someone else secretly.

The term 'heart beat pattern' is used to include heart rate but may also refer other kinds of physiological observations made on the heart. For example, instead of heart rate, the 'heart beat pattern' may be a peak to peak magnitude.

While there has been described in the foregoing description preferred embodiments of the present invention, it will be understood by those skilled in the technology concerned that many variations or modifications in details of design, construction or operation may be made without departing from the scope of the present invention as claimed. For example, It is within the contemplation of this invention that a camera is provided within the ear bud for recording and identifying unique ear canal blood vessels for biometrically identifying the person, and for also for observing light transmission into the ear canal for physiological data such as heart rate.

In other words, the embodiments include a device in which a physiological monitor and a biometric identity reader are co-located to read from the same part of a living body.

The invention claimed is:

1. A device for continual physiological monitoring of and identifying a person comprising:
   a physiological monitor; and
   a biometric identity reader;
   the biometric identity reader and the physiological monitor arranged such that the biometric identity reader is capable of reading biometric information of the person and the physiological monitor is capable of reading physiological information of the person at the same time to authenticate the physiological information as being of the person;
   wherein the device is configured such that:
   when the physiological information is authenticated as being of the person, the biometric identity reader is capable of discontinuing the reading of the biometric identity of the person while the physiological monitor continues reading physiological information of the person; and
   if the physiological monitor is detected to have been moved away from the person, the device is capable of requiring the biometric identity reader to read the biometric information of the person and the physiological monitor to read the physiological information of the person at the same time again to re-authenticate the physiological information as being of the person.

2. A device for continual physiological monitoring of and identifying a person as claimed in claim 1, wherein the physiological monitor is adjacent the biometric identity reader such that the physical distance between physiological monitor and the biometric identity reader prevents the physiological monitor and the biometric identity reader from being applied separately to more than one person at the same time.

3. A device for continual physiological monitoring of and identifying a person as claimed in claim 1, wherein the physiological monitor monitors the heart beat pattern of the person.

4. A device for continual physiological monitoring of and identifying a person as claimed in claim 1, wherein the biometric identity reader is a fingerprint reader.

5. A device for continual physiological monitoring of and identifying a person as claimed in claim 1, wherein the biometric identity reader is a biometric heartbeat pattern reader.

6. A device for continual physiological monitoring of and identifying a person as claimed in claim 1, wherein the biometric identity reader and the physiological monitor are both provided in a camera.

7. A device for continual physiological monitoring of and identifying a person as claimed in claim 1, wherein the biometric identity reader is an accelerometer.

8. A method of authenticating and continual physiological monitoring of a person comprising the steps of:
   a) providing a wearable device having a physiological monitor and a biometric identity reader;
   b) reading biometric information of the person by the biometric identity reader and at the same time reading physiological information of the person by the physiological monitor;
   c) authenticating the biometric information of the person in order to accept the physiological information as belonging to the person;
   d) discontinuing the reading of biometric information of the person by the biometric identity reader while continuing the reading of physiological information of the person by the physiological monitor; and
   e) repeating the steps b) to d) if the physiological monitor is deemed to have been moved away from the person.

9. A device for continual physiological monitoring of and identifying a person as claimed in claim 1, moving away from the person is deemed when the physiological information has ceased to be detectable for a period of time.

10. A device for continual physiological monitoring of and identifying a person as claimed in claim 1, wherein the physiological monitor is a photoplethysmography sensor.

11. A method of authenticating and continual physiological monitoring of a person as claimed in claim 8, wherein the physiological monitor is deemed to have been moved away from the person when the physiological information has ceased to be detectable for a period of time.

12. A device for continual physiological monitoring of and identifying a person as claimed in claim 1, wherein the biometric identity reader and the physiological monitor are arranged such that the biometric identity reader is capable of reading biometric information of the person and the physiological monitor is capable of reading physiological information of the person from the same part of the person.

* * * * *